United States Patent [19]

Loev

[11] 3,956,341

[45] May 11, 1976

[54] 1,3,5-TRICARBO-1,4-DIHYDROPYRIDINES

[75] Inventor: Bernard Loev, Broomall, Pa.

[73] Assignee: SmithKline Corporation, Philadelphia, Pa.

[22] Filed: Feb. 21, 1974

[21] Appl. No.: 444,455

[52] U.S. Cl. .......................... 260/295.5 R; 424/263; 424/266; 260/295 R; 260/295 AM; 260/296 D; 260/297 R
[51] Int. Cl.$^2$ ........................................ C07D 211/80
[58] Field of Search .................. 260/295.5 R, 297 R

[56] References Cited

UNITED STATES PATENTS

| | | | |
|---|---|---|---|
| 3,488,359 | 1/1970 | Bossert et al. | 260/295.5 R |
| 3,511,847 | 5/1970 | Loev et al. | 260/295.5 R |
| 3,814,771 | 6/1974 | Shen et al. | 260/297 Z |

FOREIGN PATENTS OR APPLICATIONS

| | | | |
|---|---|---|---|
| 2,302,866 | 8/1973 | Germany | 260/295.5 |

OTHER PUBLICATIONS

Murakami et al., Chem. Abstracts, Vol. 79, Germ. Offen. 2,302,866, No. 105084 q, Aug. 2, 1973.

Biellmann et al., Chem. Abstracts, Vol. 75, No. 76498 n (1971).

*Primary Examiner*—Henry R. Jiles
*Assistant Examiner*—Robert W. Ramsuer
*Attorney, Agent, or Firm*—Janice E. Williams; Alan D. Lourie; William H. Edgerton

[57] ABSTRACT

N-Substituted 1,4-dihydropyridines are prepared by reaction of the corresponding N-unsubstituted 1,4-dihydropyridines with an alkyl haloformate, an acid halide or a carbamyl halide in the presence of base. These compounds have hypotensive activity.

1 Claim, No Drawings

1,3,5-TRICARBO-1,4-DIHYDROPYRIDINES

This invention relates to new N-substituted 1,4-dihydropyridines which have pharmacological activity. In particular, these compounds have hypotensive activity.

The compounds of this invention are represented by the following structural formula:

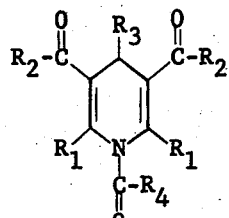

Formula I in which:

$R_1$ is lower alkyl;

$R_2$ is lower alkyl or lower alkoxy;

$R_3$ is phenyl, halophenyl, dihalophenyl, lower alkylphenyl, di-lower alkylphenyl, tri-lower alkylphenyl, lower alkoxyphenyl, di-lower alkoxyphenyl, tri-lower alkoxyphenyl, nitrophenyl, carbalkoxyphenyl, trifluoromethylphenyl, cycloalkyl, cycloalkenyl or pyridyl; and $R_4$ is lower alkyl, lower alkoxy, cycloalkyl, phenyl or di-lower alkylamino.

Preferred compounds of this invention are represented by Formula I where $R_1$ is methyl; $R_2$ is lower alkoxy; $R_3$ is trifluoromethylphenyl or halophenyl; and $R_4$ is lower alkyl, lower alkoxy or di-lower alkylamino.

Advantageous compounds of this invention are represented by Formula I where $R_1$ is methyl; $R_2$ is methoxy or ethoxy; $R_3$ is o-trifluoromethylphenyl or o-halophenyl; and $R_4$ is lower alkyl.

Particularly preferred is the compound 1,3,5-tricarbethoxy-1,4-dihydro-2,6-dimethyl-4-(2-trifluoromethylphenyl)pyridine.

As used herein the terms "lower alkyl" and "lower alkoxy" denote groups having from one to four carbon atoms, "cycloalkyl" and "cycloalkenyl" denote groups having five or six carbon atoms and "halo" refers to chloro, bromo or fluoro.

The N-substituted 1,4-dihydropyridines of Formula I are prepared by reacting the corresponding N-unsubstituted 1,4-dihydropyridines of Formula II herebelow with, when $R_4$ is lower alkoxy, an alkyl haloformate, preferably chloroformate (R'OCOX where R' is lower alkyl and X is halo); when $R_4$ is lower alkyl, cycloalkyl or phenyl, an acid halide, preferably chloride (R"COX where R" is lower alkyl, cycloalkyl or phenyl and X is halo); or when $R_4$ is di-lower alkylamino, a carbamyl halide, preferably chloride (R'''NCOX where R''' is di-lower alkyl and X is halo). The reaction is carried out in the presence of a strong base such as sodium hydride. Preferably, the reaction is carried out in a solvent such as tetrahydrofuran or dimethylformamide at from about 25°C. to the reflux temperature of the solvent, ambient temperature being preferable, for from about 15 minutes to 24 hours, 12 hours being preferable.

The N-unsubstituted 1,4-dihydropyridines which are used as starting materials for the N-substituted compounds of this invention are known to the art or are prepared by standard methods as shown below:

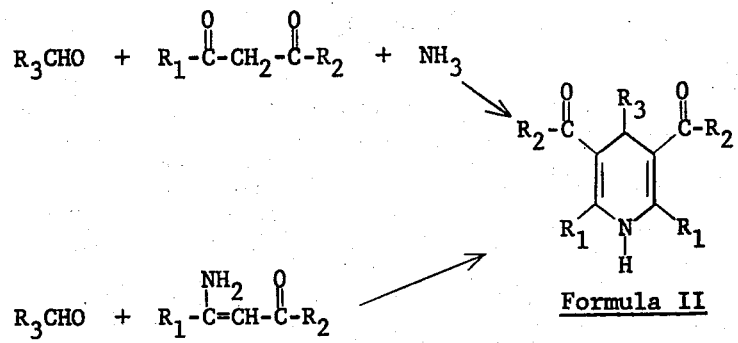

Formula II

According to procedure A, one molar equivalent of an aldehyde is reacted with two molar equivalents of the keto compound and an excess of ammonia. The reaction is preferably carried out in a solvent, such as a lower alkanol or dioxane, at elevated temperature, conveniently at reflux temperature, for about one to four hours.

According to procedure B, one molar equivalent of an aldehyde is reacted with two molar equivalents of the unsaturated amino compound. Preferably, the reaction is carried out in a solvent, such as a lower alkanol or dioxane, at elevated temperature, conveniently at reflux temperature.

Also, the compounds of Formula II are prepared by reacting one molar equivalent of an aldehyde ($R_3$CHO) with one molar equivalent of the keto compound used in procedure A and one molar equivalent of the unsaturated amino compound used in procedure B. The reaction is carried out at elevated temperature.

When $R_2$ of the keto compound from procedure A is lower alkyl, the condensation produces, in addition to the compounds of Formula II, compounds having the following isomeric structural formula:

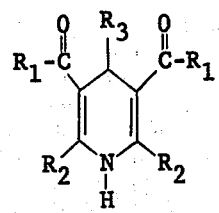

Formula III where $R_1$ and $R_3$ are as defined above and $R_2$ is lower alkyl.

Although the N-substituted dihydropyridines of this invention are drawn as having the 1,4-dihydropyridine structure, the positions of the double bonds are not known with certainty in all instances and thus it is understood that some of these compounds may hve the following 1,2-dihydrostructure (IV) in which the terms $R_1$, $R_2$, $R_3$ and $R_4$ are as defined above:

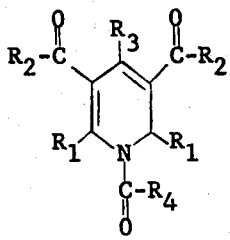

Formula IV

The hypotensive activity of the N-substituted 1,4-dihydropyridines of Formula I is demonstrated by standard procedures, that is, by intravenous administration to anesthetized cats at a dose of from about 0.01 mg./kg. to about 6.28 mg./kg. or by oral administration to metacorticoid hypertensive rats at a dose of about 80 mg./kg.

The compounds of this invention may be administered internally in conventional dosage forms, such as tablets, capsules, injectables and the like, by incorporating an appropriate effective but nontoxic dose of the compound with pharmaceutical carriers according to accepted pharmaceutical practices.

The pharmaceutical carrier may be, for example, a solid or a liquid. Exemplary of solid carriers are lactose, magnesium stearate, terra alba, sucrose, talc, stearic acid, gelatin, agar, pectin or acacia. The amount of solid carrier will vary widely but preferably will be from about 25 mg. to about 1 g. Exemplary of liquid carriers are syrup, peanut oil, olive oil, sesame oil, propylene glycol, polyethylene glycol (mol. wt. 200–400) and water. The carrier or diluent may include a time delay material well known to the art such as, for example, glyceryl monostearate or glyceryl distearate alone or with a wax.

The pharmaceutical compositions are prepared by conventional techniques involving procedures such as mixing, granulating and compressing or dissolving the ingredients as appropriate to the desired preparation.

The following examples illustrate the invention but are not to be construed as limiting the scope thereof. Temperatures are in degrees Centigrade unless otherwise indicated.

EXAMPLE 1

To 1.2 g. of sodium hydride (57% dispersion in mineral oil) suspended in tetrahydrofuran is added dropwise with stirring a solution of 10 g. of 3,5-dicarbethoxy-1,4-dihydro-2,6-dimethyl-4-(2-trifluoromethylphenyl)pyridine in tetrahydrofuran. The mixture is heated on a steam bath for 15 minutes, then it is cooled and enough dimethylformamide is added to dissolve the solid which has separated. To the resulting solution is added dropwise 3.04 g. of ethyl chloroformate and the reaction mixture is stirred at 25° for 15 minutes then heated on a steam bath for 12 hours. The mixture is filtered and concentrated to give an oil which is dissolved in acetonitrile. The solution is extracted with petroleum ether then concentrated to give an oil which is stirred with petroleum ether. The solid formed is filtered and the filtrate is concentrated in vacuo to give an oil which is chromatographed on an alumina "dry column" with methylene chloride as eluant to give 1,3,5-tricarbethoxy-1,4-dihydro-2,6-dimethyl-4-(2-trifluoromethylphenyl)pyridine, m.p. 56°–58°C.

EXAMPLE 2

When an equivalent amount of 3,5-dicarbethoxy-1,4-dihydro-2,6-dimethyl-4-(3-trifluoromethylphenyl)pyridine is substituted in the procedure of Example 1 for 3,5-dicarbethoxy-1,4-dihydro-2,6-dimethyl-4-(2-trifluoromethylphenyl)pyridine, there is obtained 1,3,5-tricarbethoxy-1,4-dihydro-2,6-dimethyl-4-(3-trifluoromethylphenyl)pyridine.

Similarly, 1,3,5-tricarbethoxy-1,4-dihydro-2,6-dimethyl-4-(4-trifluoromethylphenyl)pyridine is obtained by substitution of an equivalent amount of 3,5-dicarbethoxy-1,4-dihydro-2,6-dimethyl-4-(4-trifluoromethylphenyl)pyridine in the procedure of Example 1.

EXAMPLE 3

When an equivalent amount of a dihydropyridine listed below:
3,5-dicarbethoxy-1,4-dihydro-2,6-dimethyl-4-phenylpyridine
3,5-dicarbethoxy-4-(2-chlorophenyl)-1,4-dihydro-2,6-dimethylpyridine
3,5-dicarbethoxy-4-(2,4-dichlorophenyl)-1,4-dihydro-2,6-dimethylpyridine
3,5-dicarbethoxy-1,4-dihydro-2,6-dimethyl-4-(2,4,6-trimethylphenyl)pyridine
3,5-dicarbo-t-butoxy-1,4-dihydro-2,6-dimethyl-4-phenylpyridine
3,5-dicarbomethoxy-1,4-dihydro-2,6-dimethyl-4-(2-nitrophenyl)pyridine
3,5-dicarbomethoxy-1,4-dihydro-4-(4-methoxphenyl)-2,6-dimethylpyridine
is substituted in the procedure of Example 1 for 3,5-dicarbethoxy-1,4-dihydro-2,6-dimethyl-4-(2-trifluoromethylphenyl)pyridine there are obtained the following compounds of this invention:
1,3,5-tricarbethoxy-1,4-dihydro-2,6-dimethyl-4-phenylpyridine
1,3,5-tricarbethoxy-4-(2-chlorophenyl)-1,2-dihydro-2,6-dimethylpyridine
1,3,5-tricarbethoxy-4-(2,4-dichlorophenyl)-1,4-dihydro-2,6-dimethylpyridine
1,3,5-tricarbethoxy-1,4-dihydro-2,6-dimethyl-4-(2,4,6-trimethylphenyl)pyridine
1-carbethoxy-3,5-dicarbo-t-butoxy-1,4-dihydro-2,6-dimethyl-4-phenylpyridine
1-carbethoxy-3,5-dicarbomethoxy-1,4-dihydro-2,6-dimethyl-4-(2-nitrophenyl)pyridine
1-carbethoxy-3,5-dicarbomethoxy-1,4-dihydro-4-(4-methoxyphenyl)-2,6-dimethylpyridine.

EXAMPLE 4

Treatment of the following dihydropyridines:
3,5-dicarbomethoxy-4-(2-cyclohexenyl)-2,6-diethyl-1,4-dihydropyridine
2,6-di-n-butyl-3,5-dicarbopropoxy-4-cyclohexyl-1,4-dihydropyridine 3,5-dicarbethoxy-4-(3-cyclopentenyl)-1,4-dihydro-2,6-dimethylpyridine
3,5-dicarbethoxy-4-cyclopentyl-1,4-dihyro-2,6-dimethylpyridine
3,5-dicarbethoxy-4-(2-cyclopentenyl)-1,4-dihydro-2,6-dimethylpyridine with sodium hydride and ethyl chloroformate as described in the procedure of Example 1 gives, respectively:

1-carbethoxy-3,5-dicarbomethoxy-4-(2-cyclohexenyl)-2,6-diethyl-1,4-dihydropyridine
2,6-di-n-butyl-1-carbethoxy-3,5-dicarbopropoxy-4-cyclohexyl-1,4-dihydropyridine
1,3,5-tricarbethoxy-4-(3-cyclopentenyl)-1,4-dihydro-2,6-dimethylpyridine
1,3,5-tricarbethoxy-4-cyclopentyl-1,4-dihydro-2,6-dimethylpyridine
1,3,5-tricarbethoxy-4-(2-cyclopentenyl)-1,4-dihydro-2,6-dimethylpyridine.

EXAMPLE 5

Substitution of 3,5-dicarbethoxy-1,4-dihydro-2,6-dimethyl-4-(3-pyridyl)pyridine or 3,5-dicarbethoxy-1,4-dihydro-2,6-dimethyl-4-(4-pyridyl)pyridine in the procedure of Example 1 for 3,5-dicarbethoxy-1,4-dihydro-2,6-dimethyl-4-(2-trifluoromethylphenyl)pyridine gives 1,3,5-tricarbethoxy-1,4-dihydro-2,6-dimethyl-4-(3-pyridyl)pyridine and 1,3,5-tricarbethoxy-1,4-dihydro-2,6-dimethyl-4-(4-pyridyl)pyridine, respectively.

EXAMPLE 6

Twenty grams of 2,4-pentanedione and 17.5 ml. of ammonium hydroxide are added to 16.4 g. of methyl p-formylbenzoate in 120 ml. of ethanol and the resulting mixture is heated at reflux for five hours, then poured onto ice. The precipitated solid is filtered off and dried to give 3,5-diacetyl-4-(4-carbomethoxyphenyl)-1,4-dihydro-2,6-dimethylpyridine.

Treatment of 3,5-diacetyl-4-(4-carbomethoxyphenyl)-1,4-dihydro-2,6-dimethylpyridine with ethyl chloroformate by the procedure of Example 1 gives 3,5-diacetyl-1-carbethoxy-4-(4-carbomethoxyphenyl)-1,4-dihydro-2,6-dimethylpyridine.

EXAMPLE 7

Reaction of 2,4-hexanedione, benzaldehyde and ammonium hydroxide as described in the procedure of Example 6 gives a mixture of 3,5-diethylcarbonyl-1,4-dihydro-2,6-dimethyl-4-phenylpyridine and 3,5-diacetyl-2,6-diethyl-1,4-dihydro-4-phenylpyridine which is separated by fractional crystallization or "dry-column" chromatography on alumina.

Treatment of 3,5-diethylcarbonyl-1,4-dihyro-2,6-dimethyl-4-phenylpyridine with ethyl chloroformate by the procedure of Example 1 gives 1-carbethoxy-3,5-diethylcarbonyl-1,4-dihydro-2,6-dimethyl-4-phenylpyridine.

Similarly, treatment of 3,5-diacetyl-2,6-diethyl-1,4-dihydro-4-phenylpyridine with ethyl chloroformate by the procedure of Example 1 gives 3,5-diacetyl-1-carbethoxy-2,6-diethyl-1,4-dihydro-4-phenylpyridine.

In like manner, when 5-methyl-2,4-hexanedione, benzaldehyde and ammonium hydroxide are reacted by the procedure of Example 6 and the product 1,4-dihydropyridines obtained are separated and subsequently treated with ethyl chloroformate as described above, there are prepared 1-carbethoxy-1,4-dihydro-2,6-dimethyl-4-phenyl-3,5-diisopropylcarbonylpyridine and 3,5-diacetyl-1-carbethoxy-1,4-dihydro-4-phenyl-2,6-diisopropylpyridine.

Similarly, reaction of 5,5-dimethyl-2,4-hexanedione, benzaldehyde and ammonium hydroxide by the procedure of Example 6 with separation of the 1,4-dihydropyridines thus obtained and subsequent treatment with ethyl chloroformate as described above gives 3,5-di-t-butylcarbonyl-1-carbethoxy-1,4-dihydro-2,6-dimethyl-4-phenylpyridine and 3,5-diacetyl-2,6-di-t-butyl-1-carbethoxy-1,4-dihydro-4-phenylpyridine.

EXAMPLE 8

When a mixture of one equivalent of ethyl acetoacetate and 0.5 equivalent of a substituted benzaldehyde listed below:
2-bromobenzaldehyde
2,4-dimethylbenzaldehyde
m-tolualdehyde
3,5-dimethoxybenzaldehyde
2,4,6-trimethoxybenzaldehyde is heated under reflux in a methanol solution containing an excess of one equivalent of ammonia for 4 hours, the following 1,4-dihydropyridines are obtained upon cooling and collecting the product by filtration:

4-(2-bromophenyl)-3,5-dicarbethoxy-1,4-dihydro-2,6-dimethylpyridine
3,5-dicarbethoxy-1,4-dihydro-2,6-dimethyl-4-(2,4-dimethylphenyl)pyridine
3,5-dicarbethoxy-1,4-dihydro-2,6-dimethyl-4-(m-tolyl)pyridine
3,5-dicarbethoxy-1,4-dihydro-4-(3,5-dimethoxyphenyl)-2,6-dimethylpyridine
3,5-dicarbethoxy-1,4-dihydro-4-(2,4,6-trimethoxyphenyl)-2,6-dimethylpyridine.

Treatment of the N-unsubstituted 1,4-dihydropyridines listed above with ethyl chloroformate as described in Example 1 gives the following compounds of this invention:

4-(2-bromophenyl)-1,3,5-tricarbethoxy-1,4-dihydro-2,6-dimethylpyridine
1,3,5-tricarbethoxy-1,4-dihydro-2,6-dimethyl-4-(2,4-dimethylphenyl)pyridine
1,3,5-tricarbethoxy-1,4-dihydro-2,6-dimethyl-4-(m-tolyl)pyridine
1,3,5-tricarbethoxy-1,4-dihydro-4-(3,5-dimethoxyphenyl)-2,6-dimethylpyridine
1,3,5-tricarbethoxy-1,4-dihydro-4-(2,4,6-trimethoxyphenyl)-2,6-dimethylpyridine.

EXAMPLE 9

When an equivalent amount of methyl chloroformate is substituted in the procedure of Example 1 for ethyl chloroformate, 3,5-dicarbethoxy-1-carbomethoxy-1,4-dihydro-2,6-dimethyl-4-(2-trifluoromethylphenyl)pyridine is obtained.

Likewise, substitution of an equivalent amount of propyl chloroformate in the procedure of Example 1 for ethyl chloroformate gives 3,5-dicarbethoxy-1-carbopropoxy-1,4-dihydro-2,6-dimethyl-4-(2-trifluoromethylphenyl)pyridine.

Using butyl chloroformate in place of ethyl chloroformate in the procedure of Example 1 gives 3,5-dicarbethoxy-1-carbobutoxy-1,4-dihydro-2,6-dimethyl-4-(2-trifluoromethylphenyl)pyridine.

In like manner, the 1-carbomethoxy, 1-carbopropoxy and 1-carbobutoxy derivatives of the other N-unsubstituted dihydropyridines mentioned in the above examples are obtained.

EXAMPLE 10

Substitution of an acid chloride listed below:
acetyl chloride
valeryl chloride
benzoyl chloride
cyclohexanecarbonyl chloride
cyclopentanecarbonyl chloride
in the procedure of Example 1 for ethyl chloroformate gives the following compounds of this invention, respectively:
  1-acetyl-3,5-dicarbethoxy-1,4-dihydro-2,6-dimethyl-4-(2-trifluoromethylphenyl)pyridine
  3,5-dicarbethoxy-1,4-dihydro-2,6-dimethyl-4-(2-trifluoromethylphenyl)-1-valerylpyridine
  1-benzoyl-3,5-dicarbethoxy-1,4-dihydro-2,6-dimethyl-4-(2-trifluoromethylphenyl)pyridine
  3,5-dicarbethoxy-1-cyclohexanoyl-1,4-dihydro-2,6-dimethyl-4-(2-trifluoromethylphenyl)pyridine
  3,5-dicarbethoxy-1-cyclopentanoyl-1,4-dihydro-2,6-dimethyl-4-(2-trifluoromethylphenyl)pyridine.

In a similar manner, using the acid chlorides listed above and the N-unsubstituted dihydropyridines mentioned in the above examples, the corresponding 1-substituted 1,4-dihydropyridines of this invention are obtained.

EXAMPLE 11

When dimethylcarbamyl chloride or diethylcarbamyl chloride is substituted in the procedure of Example 1 for ethyl chloroformate, there are prepared 3,5-dicarbethoxy-1,4-dihydro-2,6-dimethyl-1-dimethylcarbamyl-4-(2-trifluoromethylphenyl)pyridine and 3,5-dicarbethoxy-1-diethylcarbamyl-1,4-dihydro-2,6-dimethyl-4-(2-trifluoromethylphenyl)pyridine.

Likewise, the 1-dimethylcarbamyl and 1-diethylcarbamyl derivatives of the other N-unsubstituted 1,4-dihydropyridines mentioned in the examples hereinabove are prepared.

What is claimed is:
1. The compound 1,3,5-tricarbethoxy-1,4-dihydro-2,6-dimethyl-4-(2-trifluoromethylphenyl)pyridine.

* * * * *

UNITED STATES PATENT AND TRADEMARK OFFICE
CERTIFICATE OF CORRECTION

PATENT NO. : 3,956,341
DATED : May 11, 1976
INVENTOR(S) : Bernard Loev

It is certified that error appears in the above-identified patent and that said Letters Patent are hereby corrected as shown below:

Column 3, line 7, "hve" should read -- have -- .

Column 4, line 42, "4-methox-" should read -- 4-methoxy-- -- .

Signed and Sealed this

Seventh Day of September 1976

[SEAL]

Attest:

RUTH C. MASON
*Attesting Officer*

C. MARSHALL DANN
*Commissioner of Patents and Trademarks*